(12) United States Patent
Reed et al.

(10) Patent No.: US 6,267,926 B1
(45) Date of Patent: Jul. 31, 2001

(54) DEVICE FOR REMOVING ENTRAINED GASES FROM LIQUIDS

(75) Inventors: Bradley W. Reed, Gastonia; Martin J. Weinstein, Charlotte, both of NC (US)

(73) Assignee: Celgard Inc., Charlotte, NC (US)

( * ) Notice: Subject to any disclaimer, the term of this patent is extended or adjusted under 35 U.S.C. 154(b) by 0 days.

(21) Appl. No.: 09/168,632

(22) Filed: Oct. 8, 1998

(51) Int. Cl.[7] ............ A61M 1/14; A61M 37/00; A61M 1/34; B01D 24/00
(52) U.S. Cl. ............ 422/48; 422/44; 604/5.01; 604/4.01; 604/6.09; 210/314; 210/435
(58) Field of Search ............ 604/4.01, 6.1, 604/5.01, 6.09, 6.11, 6.14; 422/44–48; 210/314, 348, 406, 435, 439, 446, 499

(56) References Cited

U.S. PATENT DOCUMENTS

| | | | |
|---|---|---|---|
| Re. 32,711 | * | 7/1988 | Dickens et al. ............ 210/304 |
| 3,896,061 | * | 7/1975 | Tanzawa et al. ............ 264/49 |
| 4,268,279 | * | 5/1981 | Shindo et al. ............ 55/16 |
| 4,336,224 | * | 6/1982 | Siposs ............ 422/46 |
| 4,572,724 | * | 2/1986 | Rosenberg et al. ............ 55/159 |
| 4,676,771 | * | 6/1987 | Henke ............ 604/4 |
| 5,152,964 | | 10/1992 | Leonard . |
| 5,162,102 | * | 11/1992 | Nogawa et al. ............ 422/48 |
| 5,312,479 | * | 5/1994 | Weinstein et al. ............ 96/178 |
| 5,489,413 | | 2/1996 | Carson et al. . |
| 5,501,663 | | 3/1996 | Hattler et al. . |
| 5,632,894 | * | 5/1997 | White et al. ............ 210/436 |
| 5,707,356 | | 1/1998 | Paul . |
| 5,738,645 | | 4/1998 | Plotkin . |
| 5,876,604 | * | 3/1999 | Nemser et al. ............ 210/634 |

FOREIGN PATENT DOCUMENTS

| | | |
|---|---|---|
| 0 507 722 A1 | 10/1992 | (EP) . |
| 0 713 709 A2 | 5/1996 | (EP) . |
| WO 96/24397 | 8/1996 | (WO) . |
| WO99/32186 | 7/1999 | (WO) . |

OTHER PUBLICATIONS

Polystanas: The SAFE II Oxygenating System is manufactured by: Polystan AS.8 Walgerholm DK–3500 Vaerlose Denmark "Hollow Fibre Oxygenator With Filtered Hardshell Reservoir"; Sales Brochure.

COBE Laboratories, Inc. 1993 "COBE Optima™ Hollow Fiber Membrane Oxygenator"; Sales Brochure, 1993.

Sorin Biomedical, Inc.; LC45–5000 (Rev. 2/94) "With the Monolyth, Superior Performance is a Matter of Course"; Sales Brochure, 1994.

* cited by examiner

*Primary Examiner*—Angela D. Sykes
*Assistant Examiner*—Patricia M Bianco
(74) *Attorney, Agent, or Firm*—Robert H. Hammer III

(57) ABSTRACT

An apparatus and method for removing entrained gases from a liquid by directing a liquid flow adjacent a substantially hydrophobic microporous membrane material and providing a negative pressure to one side of the membrane material to draw undissolved gas bubbles out of the liquid and through the membrane walls.

11 Claims, 2 Drawing Sheets

DEVICE FOR REMOVING ENTRAINED GASES FROM LIQUIDS

FIELD OF THE INVENTION

The present invention relates to a method and apparatus for removing entrained gases from a liquid stream. More specifically, the present invention relates to removing entrained oxygen and other gases present as micro-emboli from a blood stream during blood oxygenation and other procedures.

BACKGROUND OF THE INVENTION

The danger of unwanted air emboli persists in many medical procedures. Before fluid can safely be introduced into the body, entrained gases must be removed. Certain procedures such as blood oxygenation present the risk of embolism. However such procedures have become routine in the operating room. Blood oxygenation is required whenever heart or lung surgery is being conducted, or when a blood stream is directed to an extracorporeal treatment circuit. During open heart surgery, for example, the natural cardiovascular function of the heart and lungs is suspended. The blood is then oxygenated artificially to replace the contained carbon dioxide.

Many types of blood oxygenators are known. One type, known as a membrane oxygenator, comprises first and second conduits separated by a gas transfer membrane permeable to oxygen and carbon dioxide. Oxygen bubbles, or emboli, are undesirable in such systems. However, such entrained gases often are present in the oxygenator circuit and adversely impact on apparatus set up time. For example, some commercially available blood oxygenator circuits have priming times of up to one hour. During oxygenator setup, initial oxygenator priming is done with saline priming solution. Air bubbles may be present in the priming circuit. Therefore, one goal during priming is the removal of gas bubbles in the line.

However, the danger of bubble formation in oxygenation circuits is not restricted to priming. For example, bubbles may be formed and enter the oxygenator circuit during an operation due to bad connections in the blood circuit, by suction of blood and debris from the chest cavity, or the improper set up of the oxygenator or pressure drop through the blood circuit.

Devices are known to address these embolism problems. One class of known devices uses density gradients and gravity to separate relatively large emboli. As the gas bubbles, once separated from the fluid flow, agglomerate and rise upward in fluid flow, ball valve or bubble trap devices effectively remove large emboli from the flow. Some known bubble traps use a non-woven material encasing a foam core which disengages bubbles from the blood flow. The bubbles, once separated from the fluid flow, agglomerate and rise to the top of the trap, and are vented. However, these devices do not remove emboli smaller than the mesh openings. In addition, the priming time with these devices is still unduly long, up to about one hour.

SUMMARY OF THE INVENTION

The present invention provides a method for removing entrained gases in liquids. According to one embodiment, an arterial filter is provided having at least one vacuum port with a vacuum attached to the membrane to provide a negative pressure to increase the liberation and removal of entrained gases from a fluid being introduced to a body.

In a further embodiment, a method is provided for removing entrained gases from a liquid wherein a substantially airtight interconnected liquid circuit is provided for circulating liquid therethrough. A membrane is provided having tubular microporous membrane segments or filaments. The membrane is oriented in a housing having an inlet, an outlet and at least one vacuum port, with the membrane filaments providing a flow through channel for the liquid, extending from the inlet to the outlet. A vacuum is adapted to the vacuum port to provide a negative pressure to the circuit. The entrained gases, usually in the form of undissolved gas bubbles, are withdrawn from the fluid across the filament membranes in the direction of the vacuum and out of the circuit.

A still further embodiment of the present invention provides an apparatus for removing entrained gases from a fluid, the apparatus having a hydrophobic membrane in communication with a negative pressure environment provided by a vacuum.

A further embodiment provides an arterial filter for removing entrained gases from a liquid. The device has a housing with an inlet and an outlet. A tubular hollow membrane array extends substantially from the inlet to the outlet and is adapted to receive and direct a blood flow through the housing. A vacuum port communicates through the housing. A vacuum is attached to the vacuum port, and is operably engaged to apply a regulateable negative pressure to the gas side of the device.

In one embodiment, the housing comprises an upper, central and lower housing each having a housing wall. The upper housing has an inlet through the housing wall. The central housing is connected to the upper housing with a vacuum port extending through the central housing wall. A tubular hollow microporous membrane array is oriented longitudinally through the central housing in fluid communication with the inlet. The array is preferably arranged into a bundle. The lower housing is in communication with the central housing and comprises an outlet through the lower housing wall. It is understood that the arterial filter of the present invention may be manufactured to have one or more segments or housings.

The present invention further provides a method for oxygenating blood by providing an interconnected liquid circuit having a blood oxygenator in the circuit. The oxygenator has a membrane having first and second sides. A blood flow is directed through the oxygenator along the first side of the oxygenator membrane with a pressurized oxygen flow directed to the second side of the oxygenator membrane to oxygenate the blood flow. The blood flow is then directed from the oxygenator to an enclosed filtering membrane array comprising a housing, a blood flow inlet, blood flow outlet, and a vacuum port extending through the housing wall. The membrane is preferably a hydrophilic microporous membrane array. The blood flow proceeds through the membrane array. A vacuum is connected to the vacuum port of the filter and negative pressure is applied to the array to remove entrained gases from the blood flow. An optional oxygen flow is provided to the blood flow across the microporous membrane via an oxygen port to minimize or eliminate loss of dissolved oxygen in the blood.

In a further embodiment, the present invention provides a method for reducing blood oxygenation priming times by operating an in-line arterial filter under negative pressure in the priming circuit to more quickly remove air bubbles from the system and provide a blood oxygenation system with a reduced risk of gas embolism.

It is to be understood that both the foregoing general description and the following detailed description are exemplary and explanatory only and are not restrictive of the invention as claimed.

BRIEF DESCRIPTION OF THE DRAWINGS

Figure 1:
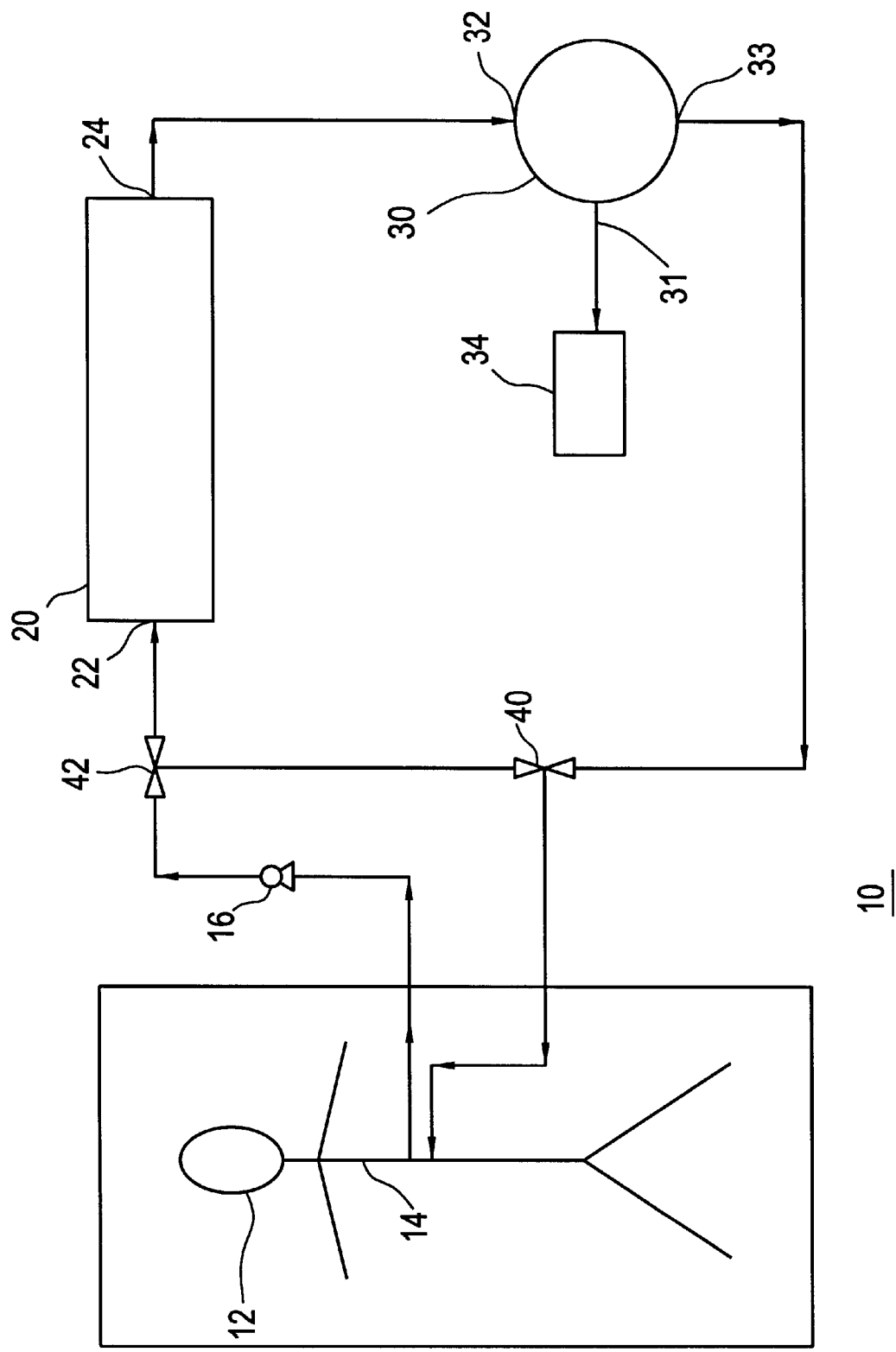
Figure 2:
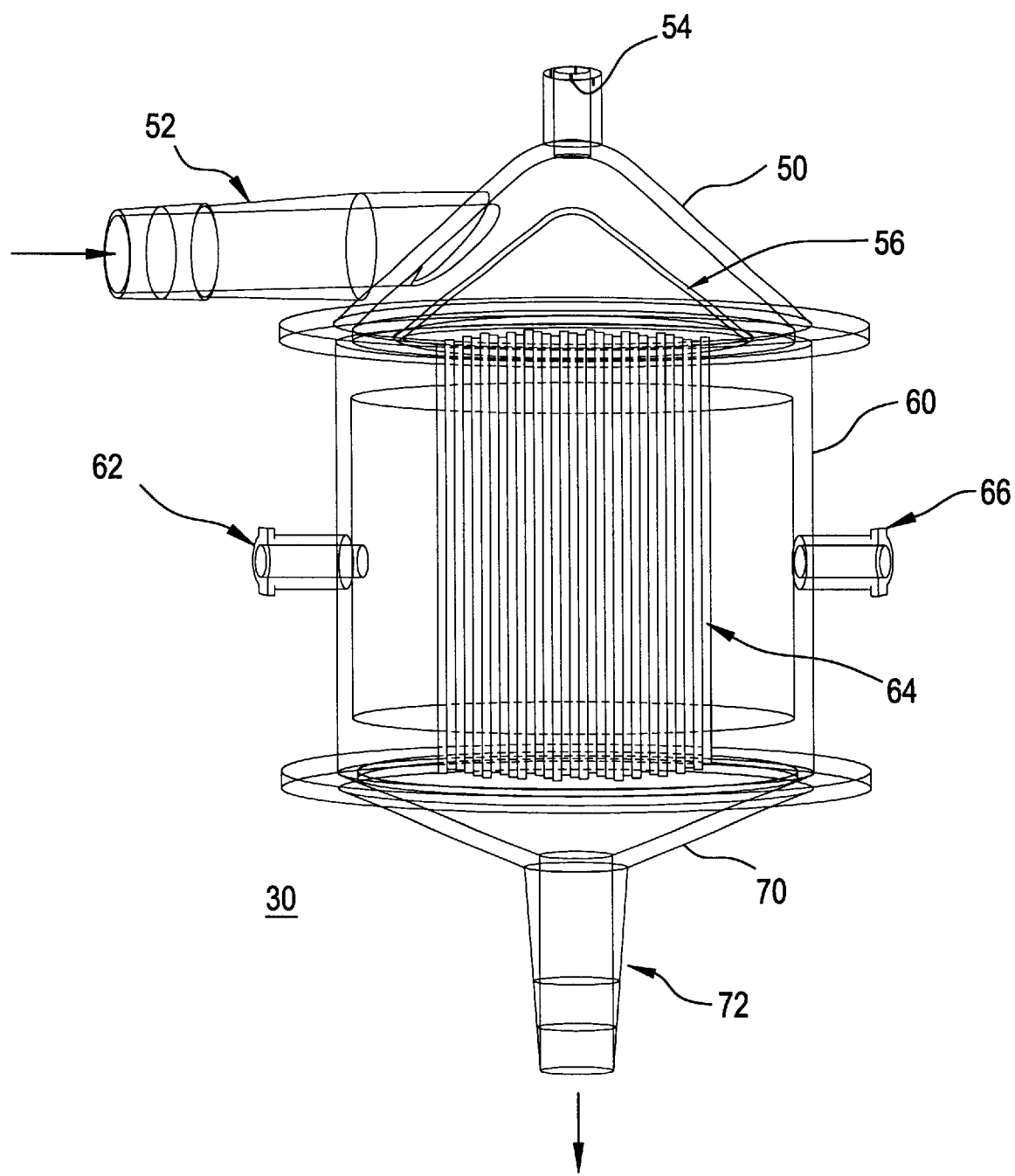

Having thus described the invention in general terms, reference will now be made to the accompanying drawings, which are not necessarily drawn to scale, and wherein:

FIG. 1 is a schematic representation of the blood oxygenation circuit of the present invention;

FIG. 2 is an exposed view of the arterial filter of the present invention;

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

According to one method of the present invention as shown in FIG. 1, a patient 12, provides a blood supply 14 that is assisted by pump 16 to an oxygenator 20 having an inlet 22 and an outlet 24. The newly oxygenated blood leaves the oxygenator and proceeds through inlet 32 of arterial filter 30. Vacuum 34 is attached to filter 30 at vacuum port 31 to provide a negative pressure to the circuit 10. In the priming sub-circuit, oxygenated blood or priming fluid such as saline is passed from the outlet 33 of filter 30 to first valve 40 in a first position directing the fluid flow to second valve 42 to oxygenator 20 until no bubbles remain in the fluid. After priming, blood flow runs to the oxygenator 20 from the patient through redirected valve 42 moved to a second position, and blood from the arterial filter returns through valve 40 moved to a second position to direct the blood flow back to the patient 12.

FIG. 2 shows an exposed view of the preferred arterial filter 30. The filter comprises upper housing 50, main housing 60 and lower housing 70. The upper housing 50 comprises inlet 52, purge port 54 and filtering screen 56. Main housing 60 comprises vacuum port 62, membrane 64, and oxygen port 66. Lower housing 70 comprises outlet 72. In operation, fluid and vacuum are separated by membrane 64. Bubbles are drawn through the membrane by the vacuum. Accordingly, fluid resides on the first side of the membrane 64 and vacuum resides on the second or other side of membrane 64.

In the priming mode of operation, filter 30 has tubing (not shown) directing a priming fluid flow such as blood plasma or, more commonly, sterile saline through the oxygenator 20. The fluid then proceeds to inlet 52 of upper housing 50 of the arterial filter. The fluid passes through a filtering screen 56. The fluid flows at a desired specified flow rate into main housing 60, along one side of membrane 64. In one preferred embodiment, the fluid does not occupy the space between the outside of the membrane 64 and the housing 60. The fluid flow is restricted to one side of the membrane (e.g. within the lumens of the hollow fibers). The low pressure created from the vacuum works to direct any bubbles present from the fluid flowing through the membrane 64 out of the system through vacuum port 62. An optional oxygen port 66 is provided. Oxygenated, but bubble-free fluid leaves the main housing 60 and passes into the lower housing 70, proceeding through outlet 72. Tubing (not shown) directs the oxygenated and bubble-free fluid back to the oxygenator 20.

Once the priming is complete, valve 40 is engaged to cut flow to the oxygenator 20 and instead directs flow to the patient 12. In this mode of operation, filter 30 has tubing (not shown) directing patient's blood (or optionally additional blood plasma) to the oxygenator 20. The oxygenator 20 may incorporate a heat exchange unit, or such temperature regulation control unit (not shown) may be placed on line remote from the oxygenator 20. Additional tubing (not shown) connects oxygenator 20 to inlet 52 of upper housing 50 of filter 30. The oxygenated blood passes through a filtering screen 56 positioned to filter out any debris, such as that produced during surgery, including clots, and any debris larger than about 20 to about 40 microns. The blood flows into main housing 60. The blood then contacts one side of membrane 64. The low pressure created from the vacuum 34 on the other side of the membrane works to direct any bubbles present in the blood flowing on the first side of the membrane 64, and out of the system through vacuum port 62. Optional air port 66 is provided. Oxygenated, but bubble-free blood leaves the main housing 60 through the membrane 64 and passes into the lower housing 70, and proceeds through outlet 72. Tubing (not shown) directs the oxygenated and bubble-free blood back to the patent 12.

The arterial filter of the present invention is designed to be retrofit to existing blood oxygenation circuits to act as a super-efficient bubble-trap. By operating the vacuum side under negative pressure, at least two benefits are effected: 1) the long priming times normally associated with blood oxygenators are significantly reduced, and 2) the filter acts as a safety bubble trap throughout the procedure to assure the safe circulation of bubble-free blood. The filters comprise a housing preferably made from relatively rigid and FDA compatible materials such as polycarbonate, polyethylene, or the like.

The vacuum-assisted arterial membranes of the present invention work to reduce priming time from the one hour time required (without the vacuum of the present invention). While the preferred embodiment presents an arterial filter having the vacuum attached thereto, it is understood that the negative pressure in combination with a microporous membrane can be applied anywhere in the system to achieve improved results with respect to decreased priming times. One likely alternate site for locating the vacuum is the oxygenator, although this presents additional complexity to the system.

While, as during oxygenation, oxygen has been pumped through such fibers to oxygenate blood across the membrane wall of the fiber, it had never been thought to apply a vacuum force to the outside surface of a hydrophobic fiber bundle while running a fluid (blood) flow through the fiber for the purpose of isolating and removing undissolved gas bubbles.

The microporous membrane of the present invention is preferably a hydrophobic membrane made from a polypropylene, polyethylene, polyurethane, polymethylpentene or polytetrafluoroethylene. Therefore, the membrane described for use in an arterial membrane filter may be any known fiber array for use in a blood oxygenator, and is preferably made from hydrophobic microporous hollow fibers made from a polypropylene material. The hydrophobicity of the membrane coupled with the negative pressure supplied by vacuum, augments the driving force of the entrained gas bubbles out of the fluid flow, through the membrane, and out of the system.

The fibers are preferably arranged in potted bundles and are in fluid communication with the arterial filter inlet port and the outlet port. In one preferred embodiment, the preferred hollow fibers are made from a polypropylene with each fiber having an outer diameter of from about 150 to about 450 microns and an inner diameter of from about 100 to about 400 microns. The packing density of the hollow fibers in the potted area is from about 30 to about 50% of the total potted area.

To construct the bundles, adhesive or resin "potting" may be used at one or both ends to position the tubular membrane bundle in the filter housing and also to form an airtight seal at each end of the housing. During the potting process, the bundles may become sealed shut. The ends of the bundles may be cut or shaved open after potting. The tubular bundles are able to withstand both positive and negative pressure. The maximum positive pressure is about 120 psig. The maximum negative pressure is about 760 mmHg.

The preferred system of the present invention contemplates the possibility that oxygen bubble removal from the blood flow could affect the desired amount of oxygen left therein. To maintain oxygen levels in the blood, an oxygen source can be provided to the membrane bundle to offset oxygen loss and maintain the saturated condition of dissolved oxygen in the blood. An oxygen source can be provided to the oxygen port or other inlet in the membrane housing. In this way, the final desired blood flow will comprise a preselected, and carefully balanced combination of blood flow rate and negative pressure applied across the tubular, hollow fiber membrane bundle, with the supplemental oxygen flow provided to the blood also across the bundle.

The vacuum applied to the system and filter of the present invention is any vacuum than can be regulated with precision to achieve negative pressures of greater than about 10 inches Hg. Particularly preferred are the commercially available or institutional vacuums having a negative pressure of from about 20 to about 25 inches Hg. It is further understood that standard vacuum sources readily available in hospital rooms and operating rooms can be used and adapted directly with the arterial filters of the present invention.

The membranes of the present invention can be any shape or dimension and can be customized to be integrated into any entrained gas removal system. It is recognized that components in such circuits may be designed to perform their intended function while requiring only very small fluid volumes. Therefore, it is understood that the membranes of the present invention may be configured to achieve a small volume such as, for example, a compressed or flat saucer-like configuration. In this configuration the number of individual tubular membranes in the membrane bundle would increase as compared to the device shown in FIG. 2. However the membrane height (bundle length) would be significantly shorter than those shown in FIG. 2. Further, the membrane may be an elongated narrow tubular membrane. In this configuration, fewer hollow membrane fibers would be needed, but the overall tubular membrane length would be longer than those shown in FIG. 2 to provide the required surface area for the oxygen bubble removal.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An arterial filter comprising:
   an upper housing having an inlet;
   a central housing in connection with the upper housing with a microporous membrane having a first side and second side, the membrane oriented longitudinally through the central housing in fluid communication with the inlet;
   a lower housing in connection with the central housing, said lower housing having an outlet in fluid communication with the membrane;
   a filtering screen disposed between said inlet and said outlet; and
   a vacuum port extending through the central housing adapted to fit a vacuum line to apply a negative pressure to the second side of the membrane.

2. The filter according to claim 1, wherein the membrane is substantially hydrophobic.

3. The apparatus according to claim 1, wherein the membrane is made from a material selected from the group consisting of: polypropylene, polyethylene, polyurethane, polymethylpentene, polytetrafluoroethylene.

4. The apparatus according to claim 1, wherein the membrane has micropores having an average diameter of from about 0.01 microns to about 0.10 microns.

5. The apparatus according to claim 1, wherein the negative pressure applied to one side of the membrane is greater than about 10 inches Hg.

6. The apparatus according to claim 1, wherein the negative pressure applied to one side of the membrane is from about 20 to about 25 inches Hg.

7. The apparatus according to claim 1, wherein the housing further comprises an oxygen inlet port to admit an oxygen flow.

8. The apparatus according to claim 7, wherein an oxygen flow having a partial pressure is regulated such that the partial pressure of oxygen in the blood is maintained.

9. The filter according to claim 1, wherein the membrane comprises tubular segments.

10. The filter according to claim 9, further comprising a plurality of tubular membranes positioned into a bundle.

11. The apparatus according to claim 2, wherein the average internal diameter of the tubular segments is from about 100 to about 450 microns.

\* \* \* \* \*